United States Patent [19]

McCrudden et al.

[11] 4,225,451
[45] Sep. 30, 1980

[54] BLEACHING COMPOSITION

[75] Inventors: Joseph E. McCrudden, Warrington; Alan Smith, Tarvin, both of England

[73] Assignee: Interox Chemicals Limited, London, England

[21] Appl. No.: 857,602

[22] Filed: Dec. 5, 1977

Related U.S. Application Data

[63] Continuation of Ser. No. 683,656, May 6, 1976, abandoned.

[30] Foreign Application Priority Data

Nov. 18, 1975 [GB] United Kingdom ............... 47372/75

[51] Int. Cl.$^2$ ....................... B05D 7/00; C11D 3/395
[52] U.S. Cl. ..................................... 252/99; 252/95; 252/102; 252/103; 252/186; 8/111; 260/502 R; 427/384; 428/403
[58] Field of Search ................... 252/95, 99, 186, 102, 252/103; 260/502, 610 R; 8/111; 427/384, 220

[56] References Cited

U.S. PATENT DOCUMENTS

| | | | |
|---|---|---|---|
| 3,983,254 | 9/1976 | Alterman et al. | 252/95 X |
| 3,992,317 | 11/1976 | Brichard et al. | 252/95 X |
| 4,006,092 | 1/1977 | Jones | 252/95 |

FOREIGN PATENT DOCUMENTS 1041983  9/1966  United Kingdom.

*Primary Examiner*—Mayer Weinblatt
*Attorney, Agent, or Firm*—Larson, Taylor and Hinds

[57] ABSTRACT

The present invention provides aromatic peroxyacids containing at least two peroxyacid groups and a total of at least three peroxyacid or carboxy acid groups, which can be incorporated in detergent or bleaching compositions.

The aromatic peroxyacids can be desensitized by intimate contact with a diluent e.g. magnesium sulphate or lauric acid, and coated to reduce destructive interaction with other components of the detergent or bleaching composition. Preferred aromatic peroxyacids include triperoxy trimellitic acid, triperoxy trimesic acid and tetraperoxy pyomellitic acid.

The aromatic peroxyacids are especialy suitable for washing white fabrics or cleaning hard surfaces, particularly at a temperature of from 30° to 60° C.

14 Claims, No Drawings

BLEACHING COMPOSITION

This is a continuation of application Ser. No. 683,656 filed May 6, 1976, now abandoned.

The present invention relates to bleaching agents and processes for bleaching.

According to the present invention there are provided bleaching agents having the general formula:

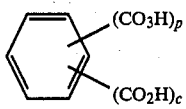

wherein $p \geq 2$ and $p+c \geq 3$, or anions thereof, the benzene nucleus being optionally substituted by a lower alkyl, chloro or nitro group.

According to a second aspect of the present invention there is provided a process for bleaching with an aqueous solution of a peroxyacid of general formula:

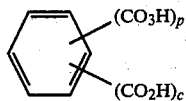

where $p \geq 2$ and $p+c \geq 3$, or anions thereof, the benzene nucleus being optionally substituted by a lower alkyl, chloro or nitro group. Preferably, the compounds have the general formula:

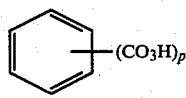

wherein $p \geq 3$ or anions thereof, the benzene nucleus being optionally substituted by a lower alkyl, chloro, or nitro group. As the number of peroxycarboxy groups substituted in the benzene ring increases, we have found that the stability of the compound tends to decrease. In consequence, the peroxyacids according to the present invention preferably contain no more than 4 peroxyacid groups.

One use of the bleaching agents described herein is in removing stains from textile fabrics. We have found that aromatic peroxyacids containing at least two peroxycarboxy groups and one or more carboxy groups tend to be less effective stain removers in alkaline solution than the corresponding peroxyacids which do not contain carboxy groups in that a given concentration of the carboxy-free compound tends to effect a higher % stain removal than the corresponding carboxy containing compound. Although we do not wish be bound by any theory, we believe that this phenomenon may be caused by electrostatic repulsion between the bleaching species and the negatively charged fabric surface. Carboxy groups have in general a much lower pKa than the peroxycarboxy groups, and hence at any given pH a higher proportion of carboxy groups will be ionised than is the case for the corresponding peroxycarboxy groups. Thus, the tendency of the molecule to be negatively charged increases as the proportion of carboxy groups increases, and hence the degree of repulsion between bleaching species and cloth increases. In consequence, preferably, the number of peroxycarboxy groups at least equals the number of carboxy groups. In several highly desirable embodiments the peroxyacid does not contain any carboxy groups.

Suitable peroxyacids include diperoxypyromellitic acid (1,4-and 1,3-isomers), diperoxyprehnitic acid (1,4-and 1,3-isomers), triperoxytrimellitic acid, triperoxytrimesic acid, triperoxyhemimellitic acid, tetraperoxypyromellitic acid and tetraperoxyprehnitic acid.

The peroxyacids described herein can be intimately contacted with a desensitising amount of a desensitising diluent, i.e. an amount which reduces the impact sensitivity sufficiently to render the composition non-hazardous. In a standard drop weight test, 30 mg of material, which has been sieved to finer than 710 microns, is placed on an anvil in the apparatus. The anvil is centred and the sample tamped lightly by a force of 5 Kg-cm. A weight is then dropped several times from a given height, each time onto a fresh sample, and its effect observed. A positive result can range from being merely a discoloured product, through emission of a cloud of smoke, to, in an extreme case, an explosion. Tests are carried out at a series of heights. A higher proportion of positive results occur when a greater force is employed. The figure usually quoted is the median point, i.e. the point at which 50% of the results at a given force are positive. Compositions having a median point of at least 200 kg.cm are considered to be non-hazardous, but to provide a greater margin of safety compositions preferably have a median point of at least 300 kg.cm. Generally the amount is within the range 0.5 to 10 parts by weight of diluent per part of peroxyacid. Suitably the desensitising diluent can be selected from hydrocarbons having melting points in excess of 30° C., e.g. microcrystalline waxes, aliphatic fatty acids e.g. lauric and stearic acids, aromatic acids e.g. benzoic acid, alkyl e.g. t-butyl esters of the aliphatic or aromatic acids, protein or starch materials boric acid and especially alkali and alkaline earth metal salts or halogen-free acids having a first dissociation constant of at least $1 \times 10^{-3}$, e.g. sodium sulphate, magnesium sulphate and sodium tripolyphosphate. The intimate contact can be by way of admixing particles of the diluent with the peroxyacid or by granulating or coating the peroxyacid with the diluent. More than one diluent may be employed, conveniently first contacting the peroxyacid with an unreactive diluent described hereinbefore, and then coating the mixture with a second diluent. Such second diluent can be selected from fatty acid alkanolamides, fatty alcohol polyglycol ethers, polyglycol/polypropylene oxide polymers alkaryl polyglycol ethers, polyethylene glycol and fatty acid esters and, amides thereof, and esters and amides of glycerol and sorbitol, polyvinyl alcohol, polymethyl methacrylate, dextrin, starch, gelatin carboxymethyl methacrylate, solid hydrocarbons, aliphatic fatty acids, fatty alcohols, sodium sulphate and magnesium sulphate. "Fatty," in the terms "fatty alcohol" and "fatty acid," is used to denote at least 12, desirably from 12 to 26 carbon atoms in the longest chain. Normally the amount of coating is within the range of 3% to 35% by weight based on the weight of the coated product. Peroxyacids thus coated are less prone to decomposition when stored in contact with alkaline surfactants, such as sodium salts of alkyl benzene sulphonates, which are commonly employed in detergent and bleaching compositions.

One convenient method of providing a desensitised composition suitable for incorporation in a detergent composition and substantially isolated from alkaline surfactants is to form a mixture of particulate peroxyacid with a particulate inorganic diluent such as sodium sulphate or tripolyphosphate or magnesium sulphate into tablets or extrudates. Such tablets or extrudates by themselves effectively reduce the surface of diacyl peroxide presented to the alkaline surfactants, and thus alleviate the problem of loss of active oxygen during storage. The problem can be further alleviated by providing an outer layer around the tablets or extrudates comprising at least one of the compounds described in the immediately preceding paragraph, generally in an amount of up to 20% by weight. Alternatively any suitable organic compound described hereinbefore may be formed into a sachet within which a desensitised composition can be placed.

Detergent or bleaching compositions containing the peroxyacids also contain a surfactant and a builder salt, often contain a processing additive and detergent adjuncts such as organic sequestrants e.g. EDTA, peroxyacid stabiliser e.g. dipicolinic acid, antiredeposition agents, perfumes, optical brightening agents and inorganic active oxygen-containing compounds, hereinfter called persalts, which generate perhydroxyl ions in aqueous solution, such as sodium perborate tetrahydrate or sodium percarbonate (the commercially available hydrogen peroxide addition product).

Suitable builder salts can be either organic, for example, aminopolycarboxylates, organic polyphosphates, sodium citrate or sodium gluconate, or inorganic, for example, alkali metal carbonates, silicates, phosphates, polyphosphates or aluminosilicates. Typically, builders are present in proportions of from 1% to 90% by weight. Such compounds alter the pH detergent/bleaching solutions. Preferably sufficient builder salt is used to obtain a solution having a pH in the range of from pH 7 to 11, more preferably from pH 8 to 11.

A typical processing aid is sodium or magnesium sulphate which is conveniently incorporated in detergent or bleaching compositions in an amount of from 1 to 40% by weight.

Where some builder salt or processing aid has been used to desensitise the diacyl peroxide the amount so used is included in the total amount of builder salt or processing aid present in the composition.

The surfactants may conventionally be water-soluble anionic, non-ionic, ampholytic or zwitterionic surface active agents. Suitable surfactants are often selected from acids and their alkali metal salts, alkyl sulphonates, alkylated aryl sulphonates, especially linear alkyl benzene sulphonates, sulphated aliphatic olefins, sulphated condensation products of aliphatic amides and quaternary ammonium compounds. The surfactants are normally present in the detergent composition in amounts of from 1% to 90% by weight, often in a weight ratio to the builder salts of from 2:1 to 1:10.

The bleaching composition can include any compound or compounds which enhance the bleaching or washing activity of organic peroxyacids, such as ketones and aldehydes as described in U.S. Pat. No. 3,822,114 or certain quaternary ammonium salts as described in British Pat. No. 1,378,671, both to Proctor & Gamble.

Generally, bleaching solutions containing the peroxyacids contain at least 1 ppm available oxygen "av. ox" and for use in washing textile fabrics e.g. cotton or polyesters often from 5 to 200 ppm. Solutions for cleaning hard surfaces such as metal, plastic or wooden surfaces can contain from 200 ppm to 500 ppm "av.ox". Peroxyacid solutions described herein can be used to bleach textile fabrics, wood and pulp and under the conditions, and employing the equipment, used for bleaching with hydrogen peroxide or inorganic peroxoacids.

Suitably, bleaching with the peroxyacids described herein can take place at an ambient temperature or higher, conveniently from 20° to 60° C. or from 25° C. to about 60° C. In general, the bleaching is effected at a controlled pH of about 8.5 to 11.5, Suitably the solutions can be produced by dissolving appropriate amounts of the detergent or bleaching compositions described hereinbefore.

Where the molecule contains an intramolecular acyl peroxide linkage, it is preferable that the molecule should be used in conjunction with, and the bleaching composition contain, at least one of the said persalts, preferably in a ratio of from 1:2 to 2:1 molecules of persalt per acyl peroxide linkage, and advantageously 1:1.

Peroxyacids described herein free of carboxy groups can be obtained by oxidising the appropriate acid with hydrogen peroxide in non-aqueous polar solvents e.g. methane sulphonic acid. In view of the inclusion of several atoms of active oxygen per molecular it is advised that great care be taken in the preparation. It is to be understood though, there where two acid groups are ortho, there is a tendency for an internal acyl peroxide to be formed instead of two peroxyacid groups, and that in consequence the full peroxyacid is generated, in situ, by perhydrolysis of the acyl peroxide. Thus oxidation of trimesic acid in methane sulphonic acid at approximately 30° C., with excess hydrogen peroxide produces triperoxytrimesic acid, but under similar conditions oxidation of pyromellitic acid produces a compound believed to contain two intra acyl peroxide linkages.

Peroxyacids containing one or more carboxyl groups can be obtained by protecting the carboxyl groups before oxidation, and employing slightly gentler oxidative conditions. Alternatively where it is desired to obtain a mixed carboxyperoxycarboxy compound where a peroxycarboxy group is orthoto a carboxy group the preparation can be effected by reacting the appropriate anhydride with hydrogen peroxide in aqueous conditions.

Specific embodiments of the present invention will now be described more fully by way of example.

The effectiveness of bleaching agents according to the present invention is compared with a conventional inorganic bleaching agent by washing stained fabrics with 1 liter water containing 4 gms of a detergent composition comprising linear alkyl benzene sulphonate 15%, sodium tripolyphosphate 37%, sodium silicate 6%, coconut monoethanolamide 3%, sodium carboxymethylcellulose 1.5%, water 6% and balance sodium sulphate, the percentages being by weight, and sufficient active oxygen containing compounds to yield 10 ppm active oxygen in solution. The washing is carried out at a temperature in the range of 30°, to 60° C. and at a pH of 9. The active oxygen containing compounds consist of (a) sodium perborate tetrahydrate, (included for comparison) (b) triperoxytrimesic acid. The fabrics comprise cotton or polyester cotton mixture, and the stains are conventional household stains. The stain removal is measured and broadly it is found that the order of stain removal is (b)>(a) in the temperature range of 30° to 60° C.

We claim:

1. A bleaching agent comprising a compound having the general formula:

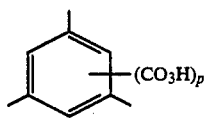

wherein $p \geq 3$, or an anion thereof, the benzene nucleus being optionally substituted by a lower alkyl, chloro or nitro group, said compound being coated with from 3% to 35% by weight of a coating agent.

2. A bleaching agent comprising a compound having the general formula:

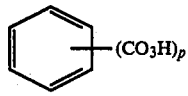

wherein $p \geq 3$, or an anion thereof, the benzene nucleus being optionally substituted by a lower alkyl, chloro or nitro group, said compound being in intimate contact with a desensitizing amount of a desensitizing diluent.

3. A bleaching agent according to claim 2 wherein the desensitizing diluent is granulated with the bleaching agent, and the granules are coated with from 3% to 35% by weight of a coating agent.

4. A bleaching or detergent composition comprising a surfactant, a builder salt and a bleaching agent, said bleaching agent comprising a compound having the general formula:

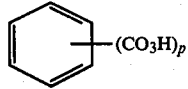

wherein $p \geq 3$ or an anion thereof.

5. An improved bleaching composition according to claim 4 wherein p is 3 or 4.

6. A bleaching or detergent composition comprising a surfactant, a builder salt, and a bleaching agent, said bleaching agent comprising a compound having the general formula:

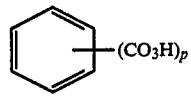

wherein $p \geq 3$, or an anion thereof, the benzene nucleus being optionally substituted by a lower alkyl, chloro or nitro group.

7. An composition according to claim 6 wherein the surfactant is present in an amount of from 1 to 90% by weight, the builder salt is present in an amount of from 1 to 90% by weight, and the bleaching agent is present in an amount of from 1 to 500 ppm available oxygen.

8. An composition according to claim 6 wherein said peroxycarboxylic acid comprises triperoxytrimesic acid.

9. An composition according to claim 6 wherein said peroxycarboxylic acid comprises triperoxytrimellitic acid.

10. A process of bleaching comprising contacting a material to be bleached with an aqueous solution comprising a peroxyacid having the general formula:

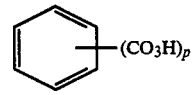

wherein $p \geq 3$, or an anion thereof, the benzene nucleus being optionally substituted by a lower alkyl, chloro or nitro group.

11. A process according to claim 10 wherein said material comprises a textile fabric and wherein the aqueous solution contains from 1 to 200 ppm available oxygen.

12. A process according to claim 10 wherein said material comprises a hard surface and wherein the aqueous solution contains from 200 to 500 ppm available oxygen.

13. A process according to claim 11 wherein the aqueous solution is maintained at a temperature of from 20° to 60° C.

14. A process according to claim 11 wherein the aqueous solution is maintained at a pH of from pH 8.5 to pH 11.5.

* * * * *